United States Patent [19]

Elson et al.

[11] 4,170,228
[45] Oct. 9, 1979

[54] VARIABLE FLOW INCENTIVE SPIROMETER

[75] Inventors: Edward E. Elson, Anaheim; Ernest L. Burke, Los Angeles; G. William Rogers, La Canada, all of Calif.

[73] Assignee: C. R. Bard, Inc., Murray Hill, N.J.

[21] Appl. No.: 739,271

[22] Filed: Nov. 5, 1976

[51] Int. Cl.² .......................... A61B 5/08; A63B 23/00
[52] U.S. Cl. ...................................... 128/725; 272/99; 73/209
[58] Field of Search ............. 128/208, 209, 210, 185, 128/188, 145.8, 142 R, 2.08, 145.6, 145.7, 195, 196, 197, 201, 202, 205, 211, 274, 276; 272/99; 73/209

[56] References Cited

U.S. PATENT DOCUMENTS

| 3,635,214 | 1/1972 | Rand et al. | 128/208 |
| 3,802,417 | 4/1974 | Lang | 128/2 R |
| 3,822,699 | 7/1974 | Cleary | 128/208 |
| 3,898,987 | 8/1975 | Elam | 128/145.8 |
| 4,025,070 | 5/1977 | McGill et al. | 272/99 |
| 4,037,595 | 7/1977 | Elam | 128/145.7 |

FOREIGN PATENT DOCUMENTS 8662 of 1903 United Kingdom ...................... 272/99

Primary Examiner—Henry J. Recla
Attorney, Agent, or Firm—Dennison, Dennison, Meserole & Pollack

[57] ABSTRACT

An incentive spirometer for breathing control exercising of post-operative patients having flow varying capability. A patient breathing tube connects through a chamber in a base and through suction tubes to the upper end of a gauge tube in which a calibrated ball having a diameter substantially the same as the gauge tube is movable. Vent means in the gauge tube below the ball allow atmospheric air to act on the lower surface of the ball so that inhalation by the patient will cause the ball to rise in the gauge tube.

5 Claims, 4 Drawing Figures

VARIABLE FLOW INCENTIVE SPIROMETER

BACKGROUND OF THE INVENTION

The present invention relates broadly to a breathing exercise device, and more specifically to an incentive spirometer for use by post-operative patients to encourage them to resume normal deep breathing. The purpose of the device is to provide motivation for the patient to make a maximum inspiratory effort and to furnish visual and/or audio feedback to show the patient how well he achieves the goals set for him.

The medical literature indicates that significant pulmonary complications occur in from 20-40% of patients following abdominal or thoracic surgery. The best evidence seems to suggest that the cause is an abnormal pattern of ventilation. Normally, a patient takes spontaneous deep breaths every five to ten minutes. This assists in achieving maximal inflation of the alveoli. If the pattern changes to a shallow, monotonous tidal ventilation, gradual alveolar collapse can occur within one hour. After several hours without such deep breathing, gross atelectasis will occur. Many post-operative patients have this shallow breathing pattern due to their generally weakened condition accompanied by pain from the incision and from the sutures.

In order to prevent or to correct the atelectasis, respiratory maneuvers must be instituted which emphasize maximal alveolar inflation as well as the maintenance of a normal functional residual capacity.

There are three basic techniques employed today to encourage deep breathing and maximal alveolar inflation. Intermittent positive pressure breathing, commonly known as IPPB, has been widely used in intensive care units of hospitals to treat and prevent atelectasis by dilating collapsed bronchi and expanding unventilated alveoli by exerting a positive pressure through the airway. The routine use of the intermittent positive pressure breathing equipment has recently come under heavy criticism and many hospitals are searching for alternative methods of treatment. Among the disadvantages of IPPB is the considerable expense of this treatment for the patient.

A technique which is now used with increasing frequency is spontaneous breathing with coaching which many feel is the ideal method because it is the closest to normal. A problem with this method is that it requires a considerable amount of time on the part of a respiratory therapist.

Incentive spirometers have been developed and these devices are used for the correction and prevention of inadequate ventilation of the alveoli due primarily to the shallow pattern of breathing following surgery as noted above. These devices have been designed to encourage patients to breathe when they might otherwise suppress their normal breathing due to pain from their incisions. Incentive spirometers are now enjoying a growing amount of popularity as an alternative to IPPB. The use of such devices is much less costly for the patient and there are fewer contraindications. If the technique is explained and taught properly to the patient by the therapist, incentive spirometers will require much less of the therapist's time since the patient can perform the breathing exercise activity on his own. The basic idea is to encourage the patient to make a prolonged inspiratory effort which he might otherwise suppress.

There are two distinct types of spirometer devices available in the market today. The first type is a simple disposable device, comparatively inexpensive, and is known as a "blow bottle." With blow bottles, the emphasis is on expiration which is exactly the opposite of what is desired. Whatever inspiration exercise obtained with these devices is achieved by the inspiration necessary for the patient to subsequently exhale. The problem present is that only a minimal expiration is required, thus making a maximal inspiration unnecessary. Accordingly, blow bottles do not meet the requirements of a good incentive device for the prevention or treatment of atelectasis, and in fact they may accomplish the opposite of what is desired.

The other type of incentive device presently available in the market is considerably more complex and expensive. These devices have some advantages over the blow bottles in the way in which they measure the number of efforts and volume achieved. There are disadvantages, however, the principal one being the initial high price and their bulky size which makes them difficult to handle. Many respiratory therapists consider these devices to be unnecessarily complicated and expensive.

SUMMARY AND OBJECTS OF THE INVENTION

It is a primary object of the present invention to provide a variable flow incentive spirometer which will enable a patient to practice proper deep breathing.

Another object of the invention is to provide a device of this general type having a variable vent means to provide a controllable variation in the inspiratory flow required of the patient.

It is a further object of the invention to provide an incentive spirometer which is inexpensive to manufacture, which may be of the disposable type, is easy to use, requiring only very simple explanation, and which is compact, small and easy to handle.

Yet another object of the invention is to provide a device of this type which will provide a wide range of inspiratory flow and will handle almost all patient conditions.

Still a further object of the invention is to provide a variable flow incentive spirometer that can be used with accessory devices, including a counter for determining the number of efforts a patient makes and the extent of such effort, or the volume achieved.

It is further contemplated that means may be provided to permit inhalation of medication through the use of the device.

An additional object of the invention is to provide an incentive spirometer incorporating a visual signal to show the patient when he achieves the volume set as his goal.

According to the invention, the device includes a base having a manifold chamber therein connected by a flexible breathing tube to a mouthpiece, through which the patient may inhale. The manifold chamber is directly connected to a pair of vertical hollow tubes, the upper ends of which are closed but which are connected by side apertures to a central cylindrical tube in which a calibrated ball or other shaped weight is vertically movable. Calibrated vent means are provided in the central tube below the center of the ball so that air at atmospheric pressure may be in contact with the lower surface of said ball.

When the patient inhales on the mouthpiece, atmospheric air enters below the ball or weight raising it because of the reduced pressure caused by the inspiration above the ball. The air above the ball will then exit through the apertures into the side tubes. An adjustable vent is provided to permit atmospheric air to be drawn into the manifold chamber, bypassing the ball to increase the effort required by the patient to raise and sustain the flow indicator ball at the top of the tube. A dial on the adjustabe vent permits a wide range of flow to permit patients with widely varying capacities to use the device.

BRIEF DESCRIPTION OF THE DRAWINGS

The invention is illustrated by way of example in the accompanying drawings which form part of this application, wherein

FIG. 3 is a vertical sectional view taken along the lines 3—3 of FIG. 1; and

DESCRIPTION OF A PREFERRED EMBODIMENT

Figure 1:
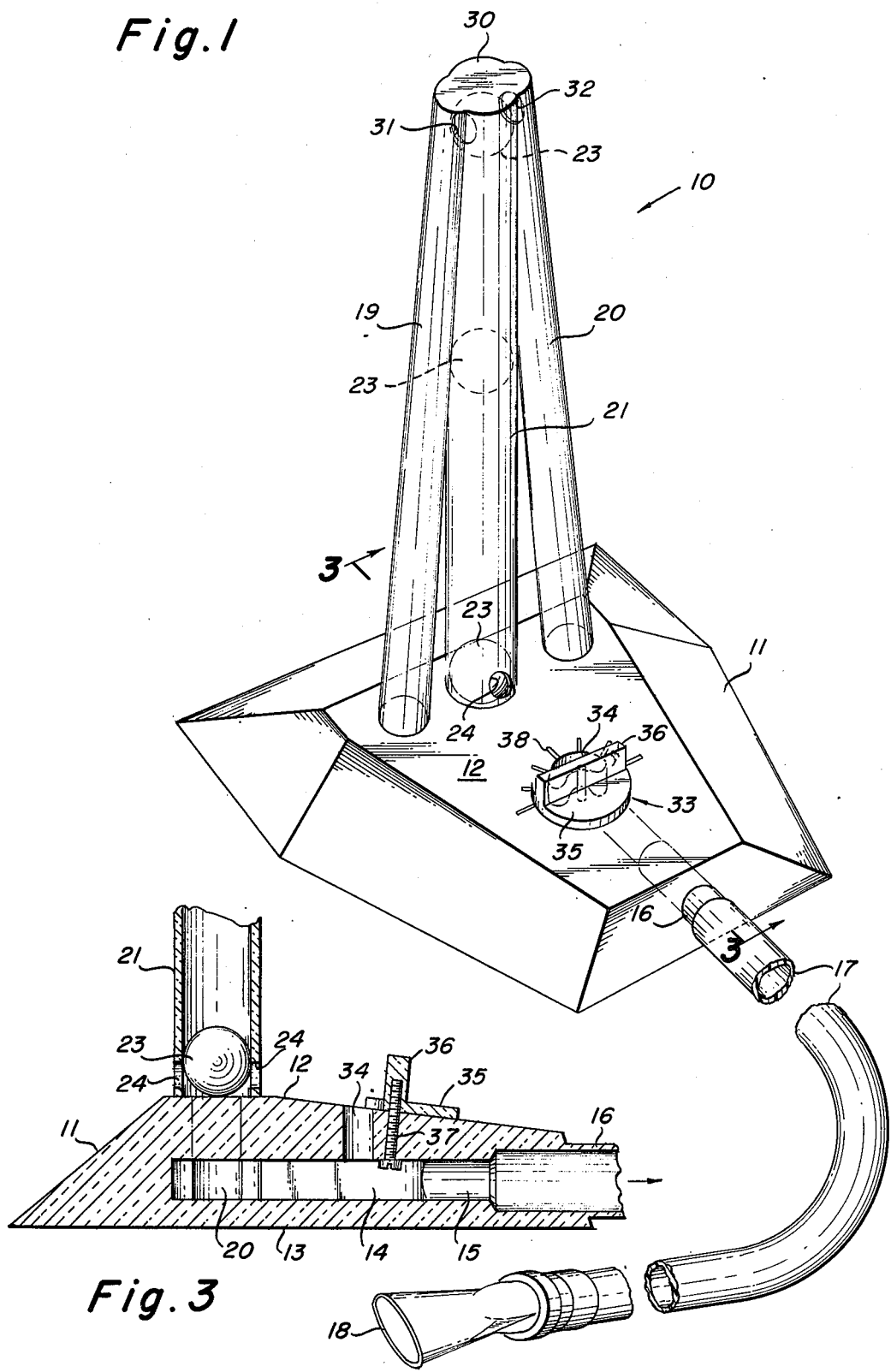
FIG. 1 is a perspective view of the variable flow incentive spirometer according to the invention with a portion of the breathing tube being cut away.

Referring now to the drawings, the incentive spirometer constituting the present invention is shown generally at 10 and includes a base member or housing 11 having a top face 12 and a flat bottom face 13. The base member may be formed in any configuration and as shown has sloped side walls to present a neat and attractive device. The base may be formed of any material, however it is contemplated that it may be injection molded from acrylic plastics.

Figure 2:
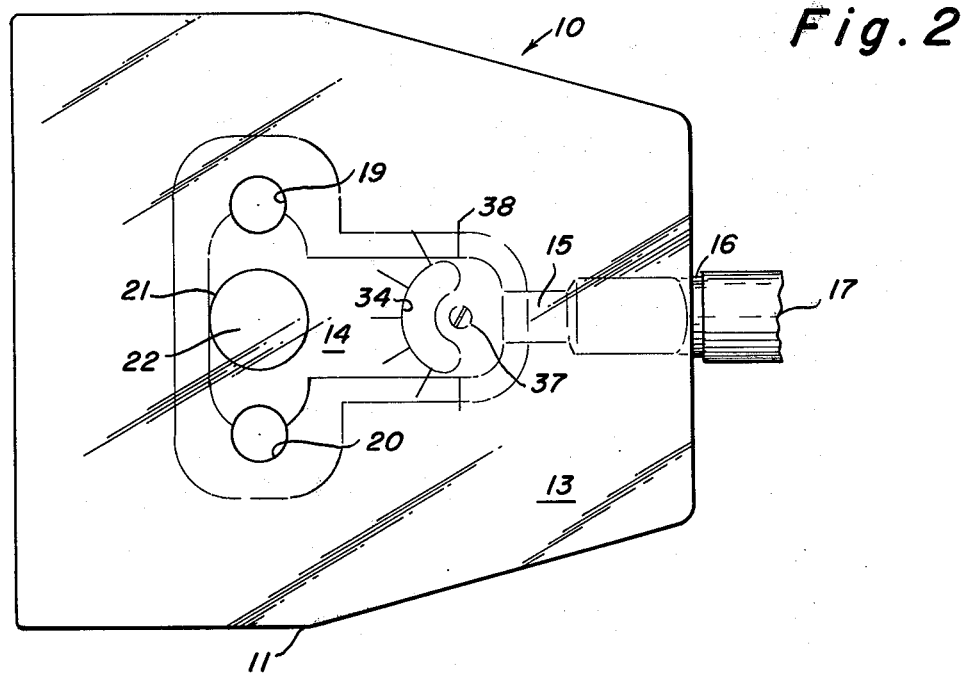
FIG. 2 is a somewhat enlarged view of the base of FIG. 1 as seen from the bottom.

A hollow manifold chamber 14 is formed in the base or housing 11. As best shown in FIG. 2, the manifold chamber is generally T-shaped. The chamber is fully enclosed and has a suction outlet opening 15 extending toward the rear of the base, terminating in a suction outlet connection nipple 16 of generally cylindrical shape. A flexible plastic breathing tube 17 may be telescopically received over the nipple 16 and serves as a conduit to the patient, terminating at its free end in a plastic mouthpiece 18 of such shape and configuration as to facilitate reception into the mouth of the patient.

In the embodiment shown, a pair of elongated rigid suction tubes 19 and 20 are mounted on the top face 12 of the base, their bottom ends being in direct open communication with the manifold chamber 14 as shown in FIG. 2. Between the suction tubes a central calibrated gauge tube 21 is provided which also extends vertically upwardly from the top face 12 although in this case the bottom surface of the gauge tube is closed off and is not in communication with the manifold chamber 14. The gauge tube 21 in the embodiment shown is closed off at the bottom by a central tube plug 22.

Preferably, at least the gauge tube is formed of a clear transparent plastic so that the patient may observe movement therein of the weight or ball 23. The weight member can consist of a spherical weight or ball 23 having a diameter very closely approaching the inner diameter of the gauge tube 21 so that there is virtually a sliding fit therebetween. Alternatively, the weight 23 may be in the form of a cylindrical sliding plug.

A calibrated atmospheric air inlet is provided for the central gauge tube as shown at 24 and in the preferred embodiment a pair of circular holes are shown. It is essential that these vent inlets be located at or below the center of the weight or ball so that the atmospheric air entering will act on the lower surface of the weight only.

As shown in FIG. 1, the ends of each of the suction tubes 19 and 20 and the central gauge tube 21 are closed by a common top cap 30. Inter-communication between the suction tubes and the gauge tube is provided by a pair of apertures 31 and 32. These apertures are preferably located just above the center line of the weight or ball 23 when it is at the top of the gauge tube. They could be just at or below the weight, but when they are above, a very slight decrease in flow will permit the ball to drop, increasing the area of the holes exposed to the air flow which thereby allows the ball to drop even more rapidly, thereby providing a good visual signal to the patient as an indication of reduced flow or effort. In addition, the holes on either side of the chamber prevent the ball from occluding the flow and thereby creating a vacuum which would tend to make the ball remain at the top. If the ball were to be held by a vacuum instead of by actual inspiration flow, a false reading would result.

In order to provide a wide range of operative conditions such as variable flow rates for different patients, and also in order to gradually increase the amount of effort required for a patient, the inspirometer includes an adjustable vent shown generally at 33 which is formed in the base 11. The vent includes a vent opening 34 extending from the top face 12 directly into the manifold chamber 14. In the preferred embodiment and as shown best in FIG. 2, the vent opening is kidney-shaped. A rotatable vent closure disc 35 is mounted on the top face of the base 11 by means of a bolt 37 which is received within the upstanding finger bar 36 of the closure disc. One side of the finger bar may serve as a dial pointer cooperating with dial indicia 38 imprinted or engraved on the top face 12 of the base. It will be apparent that rotation of the vent closure disc 35 by means of the finger bar 36 will selectively increase or decrease the size of the opening 34 which permits atmospheric air to enter the manifold chamber. The calibration of the indicia is such as to indicate the volume of air inspired and the range should preferably be between 250 to 3000 cc.

Manner of Use

Figure 4:
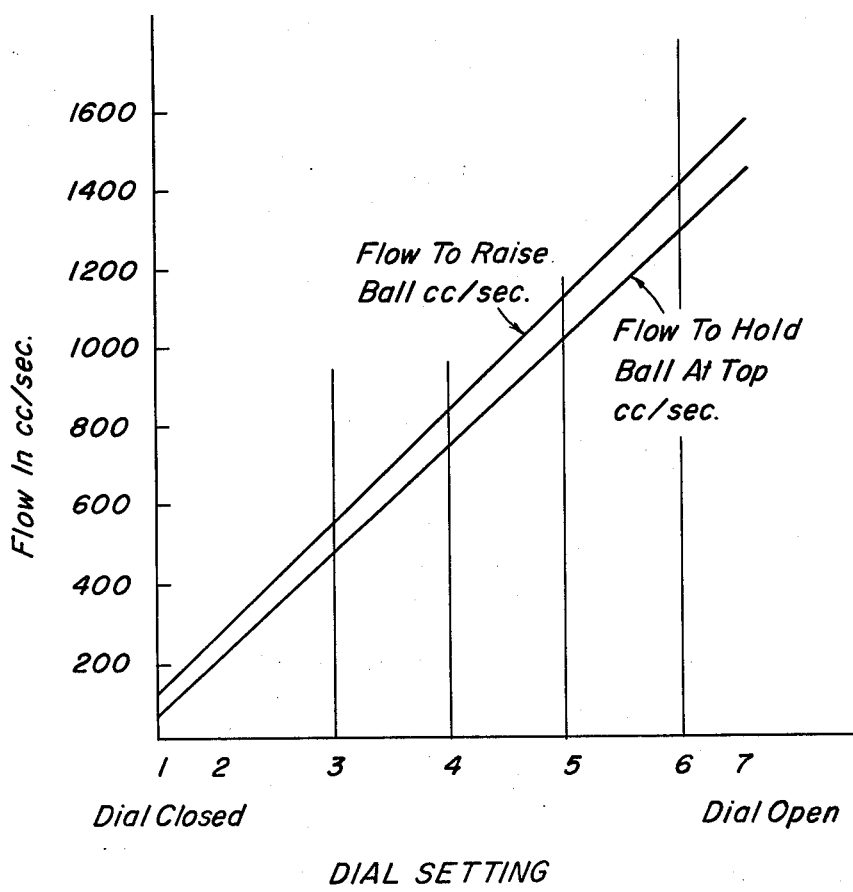
FIG. 4 is a graph comparing flow in cubic centimeters per second as opposed to dial settings of the adjustable vent.

In actual use, the patient inserts the mouthpiece 18 into his mouth and inhales deeply so that air is drawn through the mouthpiece and associated breathing tube 17. Atmospheric air enters through the calibrated air inlet 24 below the ball serving to raise it due to the reduced pressure in the gauge tube 21 above the ball. The air above the ball then exits down each of the side suction tubes 19 and 20 into the manifold chamber 14. The adjustable vent 33 permits air at atmospheric pressure to be drawn directly into the manifold chamber bypassing the ball to increase the effort required by the patient to raise and sustain the flow indicator ball at the top of the tube. As noted above, the dial permits a wide range of flows to permit patients with widely varying capacities to use the device. As shown in FIG. 4, a graph indicating the dial setting as opposed to flow in cubic centimeters is set forth, and two lines, one indicating the necessary flow to raise the ball, and the other the flow to hold the ball at the top of the gauge tube, are plotted. The flow required to raise the ball and the flow required to sustain the ball are within an average of ten percent of each other which is a desirable feature so that the therapist can chart the patient's progress.

The specific kidney shape of the vent opening in relationship to the semicircular vent closure disc 35, and the indicia 38 provide essentially linear variation as the area of the vent opening 34 is increased from one indicia line to the next.

Alternative Embodiments

Using the basic spirometer, means can be incorporated therein for counting the number of inspiratory efforts made by the patient. An automatic timer can also be provided for the purpose of ensuring that the exercise is carried out for a predetermined period.

It is also within the realm of this invention to include a volume measuring means to measure the extent of the effort made by the patient. Such a flow measuring device may be of the turbine or other conventional type known in the art. Various forms of mechanical counters can be incorporated into the device if desired to indicate the number of attempts at the exercise, the number of successful attempts, and, with modification of switch means, such counters can be used to prevent the patient from cheating or faking during the exercise.

It is also contemplated within the scope of the invention that means for providing medication may be incorporated within the inhalation flow line.

We claim:

1. A variable flow incentive spirometer comprising a housing, a manifold chamber within said housing, a breathing tube extending from said housing and being in communication with said manifold chamber, an elongated closed bottom vertical cylindrical gauge tube mounted on the top of said housing, a movable weight having a circular cross-section within said gauge tube and movable within the entire length of said gauge tube, atmospheric vent means in said gauge tube below the lowest position of the center of said movable weight, a pair of suction tubes upstanding from said housing on either side of said gauge tube and connected in fluidic communication with said manifold chamber, the upper portion of said pair of suction tubes each connected in fluidic communication with the upper portion of said gauge tube through an aperture, the entire perimeter of which is spaced below the top of said gauge tube and above the highest position therein of the center of said movable weight so that said weight cannot occlude flow between said gauge tube and suction tubes, and control vent means in communication with said manifold chamber to vary the amount of inhalation flow necessary to raise said weight means whereby inhalation effort necessary to raise said movable weight to the top of said gauge tube indicates achieving the preset inhalation flow set on said control vent means.

2. An incentive spirometer as defined in claim 1 wherein said gauge tube is cylindrical and said movable weight means is a sphere having a diameter substantially the same as said gauge tube.

3. A variable flow incentive spirometer as defined in claim 1 wherein said control vent means comprises an elongated opening extending through said housing into said manifold chamber, and a disc plate of semicircular shape rotatably mounted on said housing above said opening and adapted to selectively cover said opening.

4. A variable flow incentive spirometer as defined in claim 3 and further including indicia scale means on said housing adjacent to said opening and pointer means on said disc plate.

5. In a variable flow incentive spirometer having a housing, a manifold chamber within the housing, a breathing tube extending from the housing and being in communication with the manifold chamber, an elongated closed bottom vertical cylindrical gauge tube mounted on the top of said housing, a movable spherical weight within said gauge tube, atmospheric vent means in said gauge tube below the lowest position of the center of said spherical weight, and control vent means in communication with said manifold chamber to vary the amount of inhalation flow necessary to raise said spherical weight; the improvement comprising, a pair of suction tubes upstanding from said housing on either side of said gauge tube and connected in fluidic communication with said manifold chamber, the upper portion of said pair of suction tubes each connected in fluidic communication with the upper portion of said gauge tube through an aperture, the entire perimeter of which is located below the top thereof and above the highest position therein of the center of said spherical weight so that said weight cannot occlude flow between said gauge tube and the suction tubes, whereby inhalation effort necessary to raise said spherical weight to the top of said gauge tube indicates achieving the preset inhalation flow set on said control vent means.

* * * * *